(12) United States Patent
Boussignac

(10) Patent No.: US 8,006,697 B2
(45) Date of Patent: Aug. 30, 2011

(54) RESPIRATORY PROBE

(76) Inventor: Georges Boussignac, Antony (FR)

( * ) Notice: Subject to any disclaimer, the term of this patent is extended or adjusted under 35 U.S.C. 154(b) by 1075 days.

(21) Appl. No.: 11/814,214

(22) PCT Filed: Feb. 6, 2006

(86) PCT No.: PCT/FR2006/000261
§ 371 (c)(1),
(2), (4) Date: Jul. 18, 2007

(87) PCT Pub. No.: WO2006/090043
PCT Pub. Date: Aug. 31, 2006

(65) Prior Publication Data
US 2008/0271734 A1    Nov. 6, 2008

(30) Foreign Application Priority Data

Feb. 23, 2005 (FR) ..................................... 05 01817

(51) Int. Cl.
*A61M 11/00* (2006.01)
(52) U.S. Cl. .............................. 128/207.14; 128/207.15
(58) Field of Classification Search ............. 128/207.14, 128/207.15; 604/101, 103
See application file for complete search history.

(56) References Cited

U.S. PATENT DOCUMENTS

| 3,481,339 | A | | 12/1969 | Puig |
| 4,403,612 | A | * | 9/1983 | Fogarty .......................... 606/194 |
| 4,791,923 | A | * | 12/1988 | Shapiro .................... 128/207.15 |
| 4,976,261 | A | * | 12/1990 | Gluck et al. ............. 128/207.15 |
| 5,452,715 | A | | 9/1995 | Boussignac |
| 6,062,223 | A | * | 5/2000 | Palazzo et al. ........... 128/207.15 |

FOREIGN PATENT DOCUMENTS

| EP | 0106780 | 4/1984 |
| EP | 0640355 | 3/1995 |
| EP | 0712638 | 5/1996 |
| WO | 9966975 | 12/1999 |

OTHER PUBLICATIONS

International Search Report dated Jun. 7, 2006.

* cited by examiner

*Primary Examiner* — Steven O Douglas
(74) *Attorney, Agent, or Firm* — Dickinson Wright PLLC

(57) ABSTRACT

The invention concerns a respiratory tube (2) enclosed, at least over the major part of its length, in an inflatable flexible protective sheath (6) for isolating, from said flexible tube, the mucous membranes of the patient's airways. Further, the protective sheath (6) enables a patient to be ventilated with a breathing mixture.

5 Claims, 2 Drawing Sheets

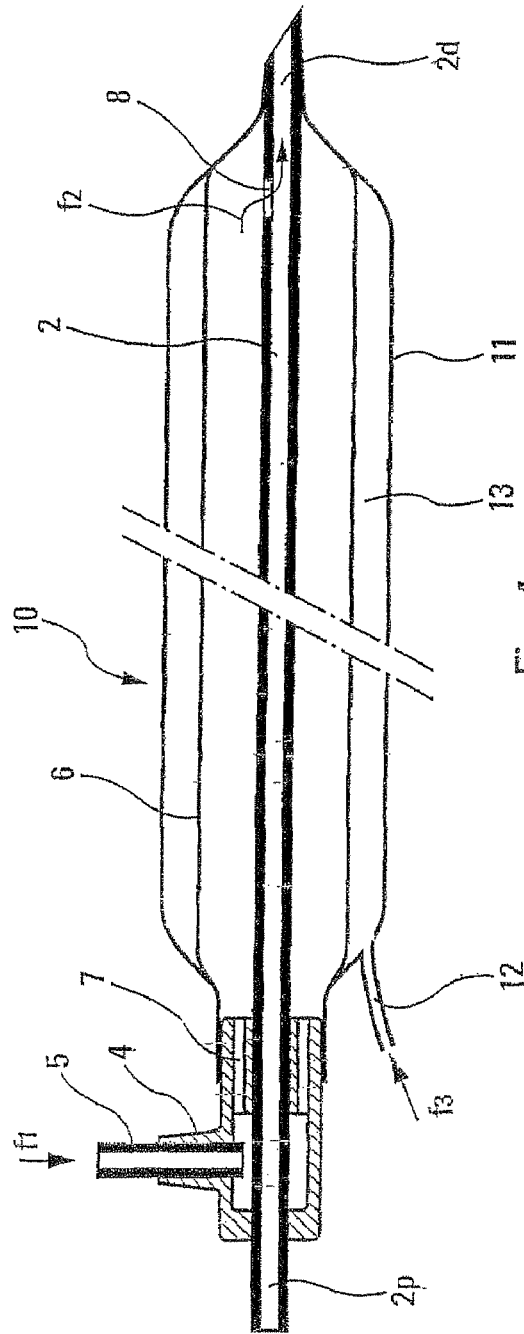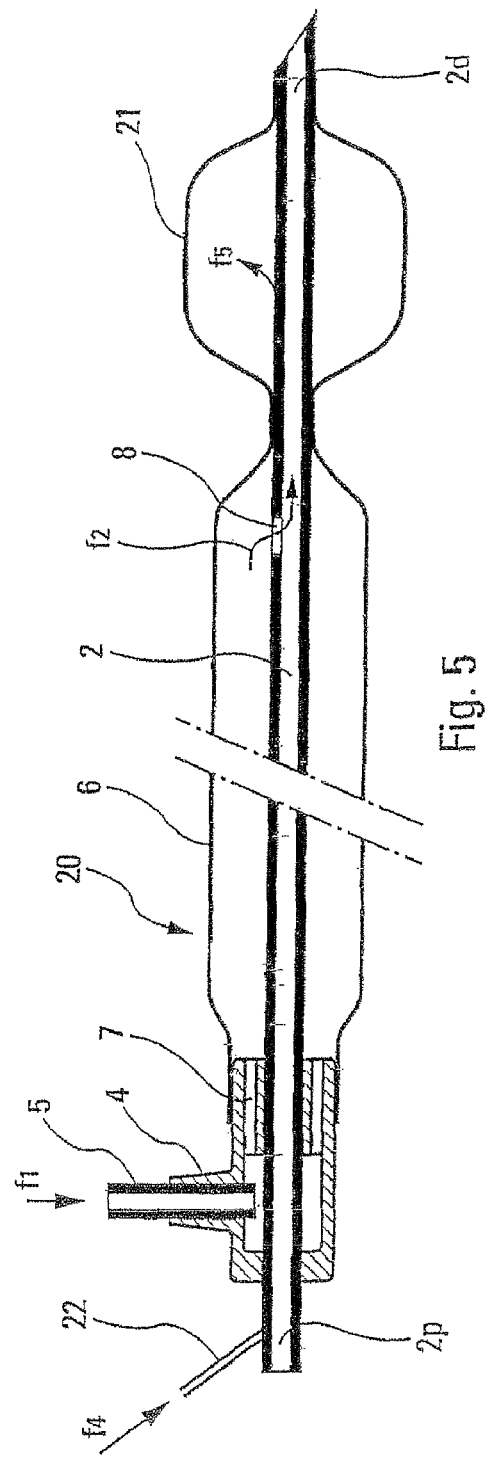

RESPIRATORY PROBE

The present invention relates to a respiratory probe comprising at least one incompressible flexible tube, for example made of a synthetic material such as a polyvinyl chloride, a polyethylene or the like, said probe being able to be introduced by the oral or nasal route into the trachea of a patient whose breathing is to be made easier or assisted.

Although not exclusively so, the probe according to the present invention is very particularly suitable for production in small dimensions in order to assist breathing in children, particularly in neonates and premature babies.

It is known that, when such a probe is in place in a patient's upper airways, said incompressible flexible tube damages the mucous membranes of these airways by rubbing against them, with the result that the probe soon becomes painful for the patient.

The object of the present invention is to overcome this disadvantage.

To this end, according to the invention, the respiratory probe comprising at least one incompressible flexible tube, able to be introduced by the oral or nasal route into the trachea of a patient, is characterized in that said tube is surrounded, at least over the greater part of its length, by at least one inflatable flexible sheath for isolating said flexible tube from the mucous membranes of said patient's airways.

Said inflatable flexible sheath can be of the same nature as the inflatable balloons that are used in some medical probes for keeping them in place in a channel of the body. However, in the present invention, said flexible sheath only has the role of protecting the mucous membranes and is not forcibly applied under pressure against these mucous membranes, as is the case of said known balloons.

It will be noted that, because of the damage they cause, the known probes are always chosen as short as possible, their distal end generally being situated at the entry to the trachea, just below the larynx. Thus, when these known probes are used to inject a respiratory assistance gas into the patient's lungs, a dead volume is present in the trachea between the distal end of the probes and the bronchi, such that some of said respiratory assistance gas cannot enter the lungs and is wasted.

By contrast, in the probe according to the invention, the length can be such that the distal end of said probe is lodged in the carina, since there is no risk of injury. The respiratory gas is then delivered directly to the bronchi, without any dead space and without any waste.

Moreover, in the known probes, it is customary to inject a respiratory gas for ventilation through channels of small diameter formed in the thickness of the wall of the probe. Of course, these known probes not only have the same disadvantages for the ventilation gas as they do for the respiratory assistance gas (dead volume, wastage), but also require said ventilation gas to be at high pressure in order to pass through said channels. It is therefore necessary to have available sources of such pressurized gas, which sources are generally cumbersome and difficult to use, and to take complex precautions to avoid damage to the patients' mucous membranes by jets of pressurized gas.

The present invention allows these additional disadvantages to be overcome, by using said inflatable protective sheath to inject the ventilation gas at low pressure. For this purpose, said protective sheath is inflated with the ventilation gas, and at least one through-passage is formed in said tube, from the distal end of the probe and inside said sheath, such that the ventilation gas inflating the sheath can pass from the latter into the inside of said tube and, from there, into the trachea of said patient.

If appropriate, especially when leaktightness is necessary between the probe and the trachea in order to avoid gastric juices from entering the patient's lungs, the respiratory probe according to the present invention can:

either comprise an additional inflatable flexible sheath that surrounds said inflatable flexible protective sheath in a leaktight manner;

or be such that said inflatable flexible protective sheath does not cover the distal end of said incompressible flexible tube, and that said distal end of said tube carries an inflatable balloon.

The figures in the attached drawing will show clearly how the invention can be realized. In these figures, identical reference signs designate similar elements.

FIGS. 4 and 5 show schematic longitudinal sections through two other illustrative embodiments of the respiratory probe according to the present invention when in the inflated state.

Figure 1:
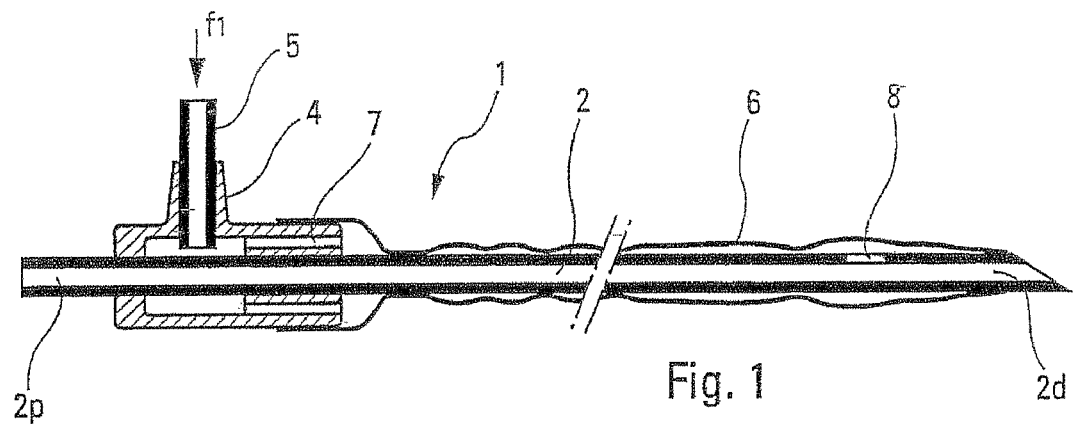
FIG. 1 is a schematic longitudinal section through an illustrative embodiment of the respiratory probe according to the present invention, the flexible protective sheath being in the deflated state.
Figure 2:
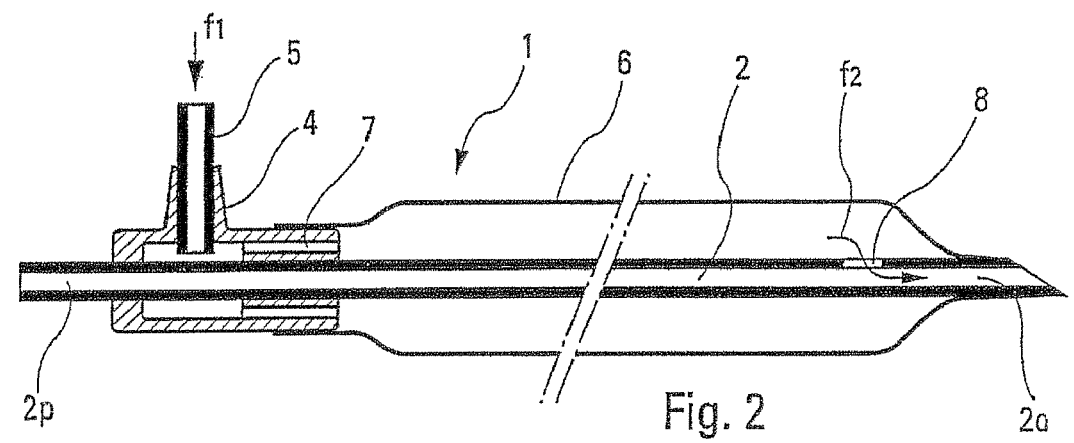
FIG. 2 is a view similar to that of FIG. 1, said flexible protective sheath being in the inflated state.

The probe 1 according to the present invention, shown by way of example in FIGS. 1 and 2, comprises an incompressible flexible tube 2, for example made of a synthetic material such as a polyvinyl chloride or a polyethylene, and provided with a distal end 2d and a proximal end 2p. The distal end 2d is intended to be placed in the carina 3 of a patient (see FIG. 3), while the proximal end 2p, outside of said patient, is connected either to the surrounding air or to a source of respiratory assistance gas (not shown).

The proximal end 2p of the flexible tube 2 is surrounded by a connector piece 4, which is provided with a conduit 5 that can be connected to a source of respiratory gas for low-pressure ventilation (symbolized by the arrow f1).

An inflatable flexible sheath 6, for example made from a plastic film measuring several tens of micrometers, surrounds the tube 2 along almost all of its length and its ends are connected in a leaktight manner on the one hand to the connector piece 4 and on the other hand to the tube 2 near the distal end 2d.

Inside the connector piece 4, channels 7 provide a communication between the conduit 5 and the inside of the inflatable flexible sheath 6. Moreover, the inside of said inflatable flexible sheath 6 communicates with the inside of the tube 2 by way of at least one hole 8 that passes through the lateral wall of said tube and that is arranged toward the distal end of said sheath.

Figure 3:
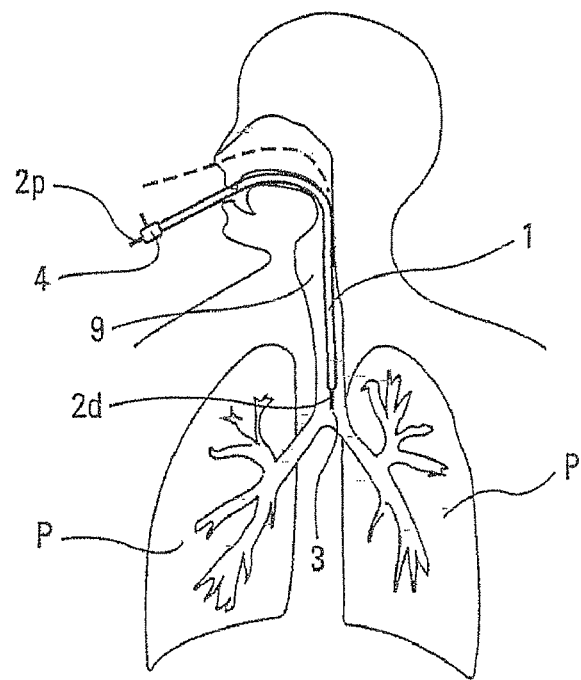
FIG. 3 is a schematic illustration of the probe from FIGS. 1 and 2 when placed in the upper airways of a patient.

The probe 1 can be introduced into the patient's trachea 9, either by the oral route (shown by solid lines in FIG. 3) or by the nasal route (broken lines in FIG. 3). In the latter case, the probe 1 can comprise two parallel tubes 2 starting from the connector piece 4 (one tube per nostril). Upon introduction, the sheath 6 is in the deflated state (FIG. 1), and the length of the probe 1 is such that the distal end 2d reaches the carina 3.

Once in place, as is indicated in FIG. 3, the conduit 5 is supplied with respiratory gas for ventilation (arrow f1) such that, on the one hand, the sheath 6 inflates (FIG. 2), thus avoiding contact between the patient's mucous membranes and the tube 2, and, on the other hand, respiratory gas passes from the sheath 6 into the tube 2 by way of the holes 8 (arrow f2). This results in respiratory gas emerging from the distal end 2d of the probe 1, in the area of the carina 3, in order to supply the patient's lungs P, without any dead space and without waste.

The patient exhales through the tube 2, from the distal end 2d to the proximal end 2p.

To ensure that said flexible sheath 6 in the inflated state (FIG. 2) assumes a predetermined shape, it is advantageous for it to be preformed.

In the embodiment variants 10 and 20 illustrated in FIGS. 4 and 5, respectively, the probe according to the present invention comprises the elements 2 and 4 to 8 described above.

The probe 10 in FIG. 4 further comprises an inflatable flexible sheath 11, which is similar to the sheath 6 and which surrounds the latter and has its ends connected in a leaktight manner on the one hand to the connector piece 4 and on the other hand to the tube 2 near the distal end 2d. At the proximal end, the flexible sheath 11 is connected to a conduit 12, by way of which an inflation gas can be introduced (symbolized by arrow f3) into the space 13 between the sheaths 6 and 11. Thus, the probe 10 is particularly comfortable for the patient, since it comprises two superposed gaseous cushions (one formed between the tube 2 and the sheath 6, and one formed between the sheath 6 and the sheath 11). Moreover, the sheath 11 can serve to ensure leaktightness between the probe 10, the carina 3 and the trachea 9, in such a way as to avoid the patient's gastric juices entering the lungs P.

In the probe 20 in FIG. 4, the sheath 6 does not cover the tube 2 as far as its distal end 2d, and the latter carries an inflatable balloon 21 in a known manner. The inflatable balloon 21 is connected, for example by way of a channel formed in the thickness of the wall of the tube 2 and not visible in FIG. 5, to a conduit 22 arranged at the proximal end of the probe 20 and able to be connected to a source of inflation gas. Thus, the gas passing through the conduit 22 (symbolized by arrow f4) can flow into the balloon 21 (arrow f5) in order to inflate the latter and thereby ensure the leaktightness between the probe 20 and the carina 3. The patient's lungs P are thus isolated from the gastric juices.

The invention claimed is:

1. A respiratory probe comprising
   at least one incompressible flexible tube, configured to be introduced by the oral or nasal route into the trachea of a patient;
   at least one inflatable flexible protective sheath for isolating said flexible tube from the mucous membranes of the patient's airways, wherein said at least one inflatable flexible protective sheath surrounds said tube at least over the greater part of its length;
   at least one through-passage formed in said incompressible flexible tube from a distal end of the probe and inside said protective sheath; and
   a conduit arranged in fluid communication with said protective sheath such that respiratory gas supplied to said conduit passes to said protective sheath for inflating the protective sheath and passes through the at least one through-passage into the trachea of said patient.

2. The respiratory probe as claimed in claim 1, wherein its length is such that, when it is in place in the patient's upper airways, its distal end is situated in the carina of the latter.

3. The respiratory probe as claimed in claim 1, wherein said flexible protective sheath is preformed in order to assume a defined inflated shape.

4. The respiratory probe as claimed in claim 1, wherein it comprises an additional inflatable flexible sheath that surrounds said inflatable flexible protective sheath in a leaktight manner.

5. The respiratory probe as claimed in claim 1, wherein said inflatable flexible protective sheath does not cover the distal end of said incompressible flexible tube, and said distal and of said tube carries an inflatable balloon.

* * * * *